United States Patent [19]
Najor

[11] Patent Number: 5,638,829
[45] Date of Patent: Jun. 17, 1997

[54] BIRTH CONTROL GARMENT

[75] Inventor: Ramsey L. Najor, San Juan Capistrano, Calif.

[73] Assignee: Ramsey Najor, San Juan Capistrano, Calif.

[21] Appl. No.: 348,586

[22] Filed: Dec. 2, 1994

[51] Int. Cl.$^6$ ........................................................ A61F 6/02
[52] U.S. Cl. ........................ 128/842; 128/844; 128/918
[58] Field of Search ............................... 128/842, 844, 128/918; 604/347–353; 602/70–73

[56] References Cited

U.S. PATENT DOCUMENTS

| | | |
|---|---|---|
| D. 288,485 | 2/1987 | Denno . |
| 3,353,538 | 11/1967 | Carrigan . |
| 3,536,066 | 10/1970 | Ludwig ................................... 128/844 |
| 4,004,591 | 1/1977 | Freimark . |
| 4,381,000 | 4/1983 | Duncan . |
| 4,488,541 | 12/1984 | Garcia . |
| 4,553,968 | 11/1985 | Komis . |
| 4,735,621 | 4/1988 | Hessel . |
| 4,807,611 | 2/1989 | Johnson . |
| 4,834,113 | 5/1989 | Reddy . |
| 4,834,114 | 5/1989 | Boarman . |
| 4,862,901 | 9/1989 | Green ..................................... 128/844 |
| 4,867,176 | 9/1989 | Lash . |
| 4,875,490 | 10/1989 | Quiroz . |
| 4,895,604 | 1/1990 | Spery . |
| 4,898,184 | 2/1990 | Skurkovich ........................... 128/844 |
| 4,942,885 | 7/1990 | Davis et al. . |
| 4,945,923 | 8/1990 | Evans et al. . |
| 4,966,165 | 10/1990 | Anderson ............................. 128/844 |
| 4,971,071 | 11/1990 | Johnson . |
| 4,981,147 | 1/1991 | Barnett ................................. 128/842 |
| 4,993,431 | 2/1991 | Reddy . |
| 5,146,930 | 9/1992 | Richardson ......................... 128/842 |
| 5,181,527 | 1/1993 | Dorsey ................................ 128/844 |
| 5,209,241 | 5/1993 | Hardy .................................. 128/844 |
| 5,269,320 | 12/1993 | Hunnicutt ........................... 128/842 |
| 5,351,699 | 10/1994 | Hammons ........................... 128/842 |

FOREIGN PATENT DOCUMENTS 2649316   1/1991   France ................................. 128/844

Primary Examiner—Michael A. Brown
Attorney, Agent, or Firm—Richard L. Myers

[57] ABSTRACT

A body garment adapted to be worn by a user having a waist and an abdominal area includes a brief having a waist band and a crotch section sized and configured to be worn over the abdominal area of the user. A tubular enclosure forms a sanitary barrier having a closed end and an opened end, an elongated state and a collapsed state. The open end is coupled to the crotch section of the brief. An envelope sealed to the brief defines a compartment to removably receive the tubular enclosure in the collapsed state. An associated method includes the step of inverting one of the brief or the tubular enclosure between a first state wherein the tubular enclosure extends inwardly of the brief in order to accommodate a female anatomy, and a second state wherein the tubular enclosure extends outwardly of the brief in order to accommodate a male anatomy.

13 Claims, 3 Drawing Sheets

BIRTH CONTROL GARMENT

BACKGROUND OF THE INVENTION

1. Field of the Invention

This invention relates generally to birth control devices and more specifically to condoms which are configured to accommodate the male anatomy and diaphragms which are configured to accommodate the female anatomy.

2. Discussion of the Prior Art

With the rapid increases in populations throughout the world there is great interest in controlling further increases, particularly in undeveloped countries. While the ultimate goal may be to prevent further population increases, the tendency is to focus on birth control; and certainly the most humane way to control birth is to prevent conception in the first place.

In the past various contraceptive devices have been proposed for placing a barrier between the penis, hereinafter referred to as the male anatomy, and the vagina, hereinafter referred to as the female anatomy. These barriers have been formed as condoms which are designed to fit the male anatomy, and diaphragms which are designed for insertion into the female anatomy. Although the condoms have been formed with a severely constricting band, they have been far superior functionally to the diaphragms which form poor seals with the female anatomy.

With this superior functional capability, the male participant has been relied on primarily to provide and use the contraceptive. While the responsibility has rested primarily on the male participant, it is the female participant who suffers the burden associated with failure to use a contraceptive. It is the female participant who must carry the fetus, deliver the baby, and sometimes single-handedly raise the child. A better contraceptive has been needed which can be administered by the female participant who carries the greatest burden of conception. A device which might be alternatively used by the male participant or female participant would be of even greater advantage.

SUMMARY OF THE INVENTION

These deficiencies of the prior art are overcome with the present invention which includes a garment in the form of a brief having a waist band and a crotch section. A tubular enclosure which can function either as a condom or diaphragm extends from the crotch section of the brief. The tubular enclosure includes a tube having a first end attached to the brief and a second end free of the brief. The tubular enclosure can be disposed in either an extended state or a collapsed state. An envelope is formed by two patches which sealingly engage opposite sides of the brief forming a compartment which is sized and configured to receive the tubular enclosure in the collapsed state. A lubricant can be disposed in the compartment of the envelope with the collapsed tubular enclosure. Both the brief and the tubular enclosure can be integrally formed from an elastomeric material. A greater thickness of the material forms a cap at the free end of the tube.

The garment can be adapted by the user to accommodate either the male anatomy or the female anatomy. This is accomplished by inverting either the brief or the tubular enclosure so that the enclosure extends inwardly to accommodate the female anatomy, or outwardly to accommodate the male anatomy.

The advantages of this garment for controlling conception are now immediately apparent. The garment can be worn at all times by a user with the tubular enclosure in the collapsed state sealed in the envelope. Thus the contraceptive device is always available to the person wearing the garment. The contraceptive can be deployed by removing the patches which form the envelope, thereby exposing the tubular enclosure for placement on the male anatomy or within the female anatomy.

Thus with the manufacture of a single garment, the responsibility for conception can be shared by both the male and female participant. The low cost of manufacture associated with this garment should make it readily available for distribution throughout the countries of the world.

In one aspect of the invention, a body garment is adapted to be worn by a user having a waist and an abdominal area. A brief is sized and configured to be worn over the abdominal area and includes a waist band and a crotch section. A tubular enclosure forming a sanitary barrier has a closed end and an open end, an elongated state and a collapsed state. The open end of the tubular enclosure is coupled to the crotch section of the brief. An envelope sealed to the brief defines a compartment which is sized and configured to removably receive the tubular enclosure in the collapsed state. In a particular embodiment, the tubular enclosure may be integral with at least the crotch section of the brief.

In a further aspect of the invention, a reversible protective garment includes a brief having a first side and a second side, and an elastomeric tube having a first end and a second end, the tube being extensible from a collapsed state to an extended state. The garment includes means for attaching the first end of the tube to the brief while a cap is disposed to fully enclose the second end of the tube. One of the tube and the brief is invertible to reverse the garment in order to alternatively accommodate a male anatomy and a female anatomy.

The method of use associated with the invention includes the steps of providing the garment with a brief having a first side and a second side. Coupling to the brief a tubular enclosure forms a sanitary barrier with a first surface and a second surface. The method includes the step of inverting one of the brief and the tubular enclosure between a first state wherein the enclosure extends inwardly of the brief in order to accommodate a female anatomy, and a second state wherein the tubular enclosure extends outwardly of the brief in order to accommodate a male anatomy.

These and other features and advantages of the invention will become more apparent with a discussion of preferred embodiments and best mode of the invention, and reference to the associated drawings.

DESCRIPTION OF PREFERRED EMBODIMENTS AND BEST MODE OF THE INVENTION

Figure 1:
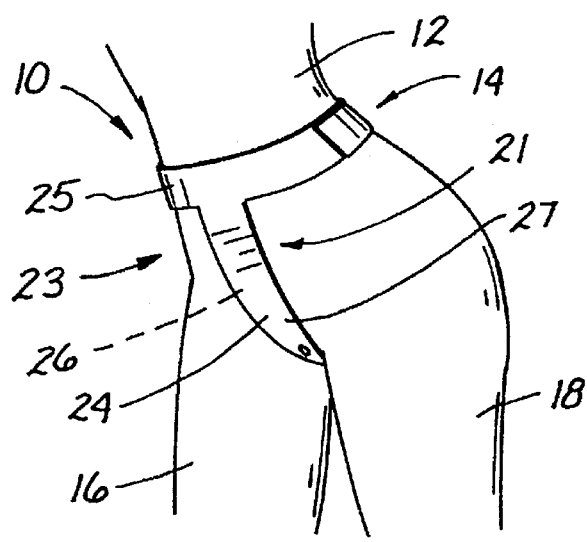
FIG. 1 is a perspective view of a preferred embodiment of the garment of the present invention operatively disposed over a female anatomy.

A garment is illustrated in FIG. 1 and designated generally by the reference numeral 10. The garment 10 is operatively disposed on a female body 12 having a waist 14 and a pair of legs 16 and 18 which define an abdominal region 21 of the body 12.

The garment 10 includes a brief 23 having a first side 24 and a second side 26. In a preferred embodiment, the brief 23 includes a waist belt 25 and a crotch section 27 which is attached to and extends downwardly from the belt 25. When the garment 10 is operatively disposed, the waist belt 25 engages the waist 14 of the body 12 while the crotch section 27 extends generally perpendicular to the belt 25 between the legs 16, 18 of the body 12.

Figure 2:
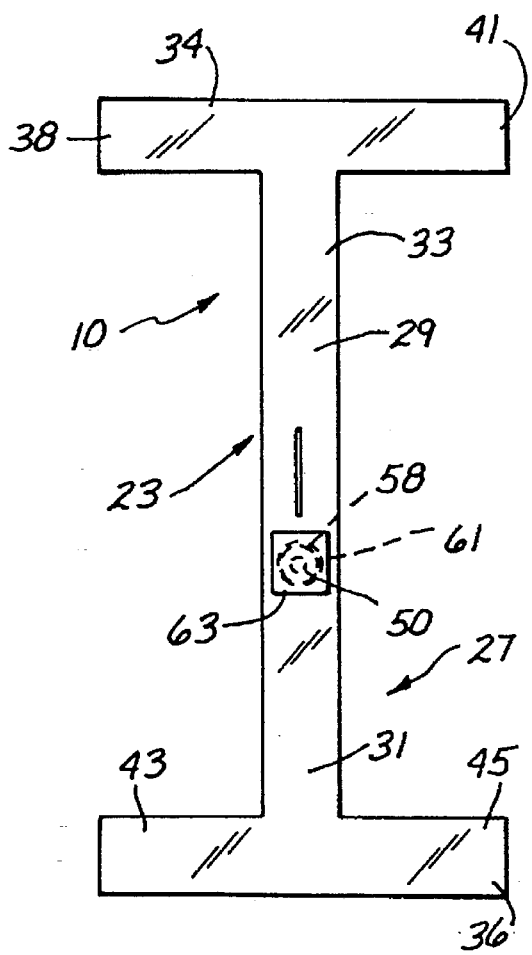
FIG. 2 is a top plan view of one embodiment of the garment including a tubular enclosure disposed within a compartment of an envelope.
Figure 3:
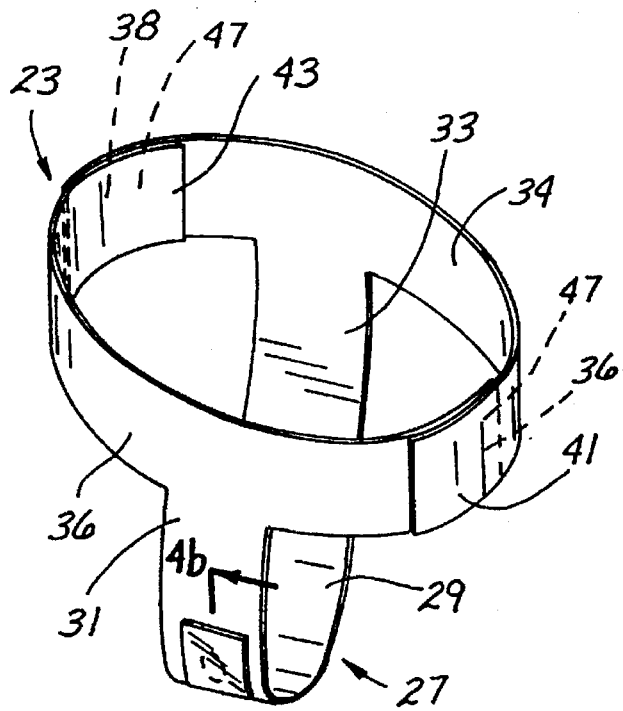
FIG. 3 is a perspective view of the garment of FIG. 2 assembled for use.

In a preferred embodiment illustrated in FIG. 2, the crotch section 27 includes an elongate crotch belt 29 which extends between opposing ends 31 and 33. The waist belt 25 is formed with two waist sections 34 and 36. The waist section 34 extends longitudinally between its ends 38 and 41 and in generally perpendicular orientation with respect to the crotch belt 29 at the end 33. Similarly, the waist portions 36 extends between its ends 43 and 45 generally perpendicular to the crotch belt 29 at the end 31. With this embodiment of the garment, the end 38 of the waist section 34 can be attached to the end 43 of the waist section 36. Similarly, the end 41 of the waist section 34 can be attached to the end 45 of the waist section 36. Preferred means for attachment include fasteners 47 such as snap fasteners or hook and loop fasteners.

Figure 4A:
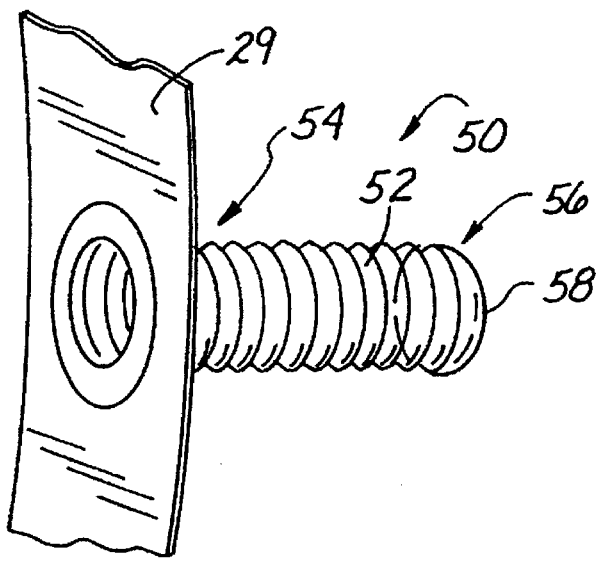
FIG. 4a is a side perspective view of the tubular enclosure disposed in an extended state.
Figure 4B:
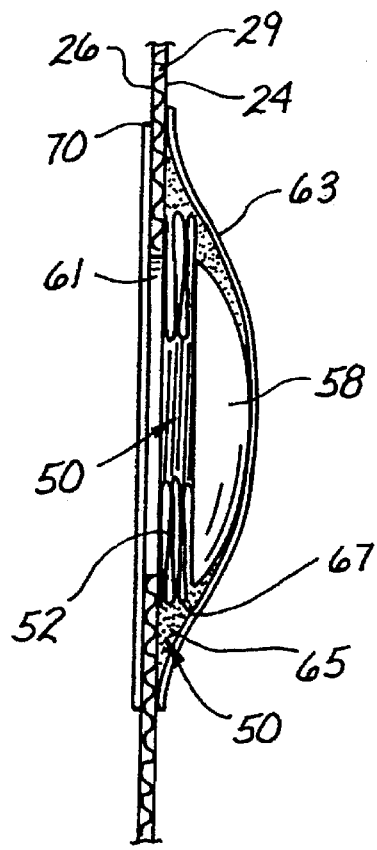
FIG. 4b is a cross section view of the envelope illustrating the tubular enclosure in a compressed state, the view being taken along lines 4b—4b of FIG. 3.

Of particular interest to the present invention is a tubular enclosure 50 which is illustrated in an extended state in FIG. 4a and in a compressed state in FIG. 4b.

In the illustrated embodiment, the tubular enclosure 50 includes a tube 52 having a first end 54 and a second end 56. The first end 54 is open and extends circumferentially in an integral relationship with the belt 29. An end cap 58 is disposed to fully close the second end 56 of the tube 52. Although the integral relationship may be preferred, in other embodiments of the invention, the first end 54 of the tube 52 can be attached to the belt 29 by a circumferential heat seal or adhesive.

In its compressed state, the tubular enclosure 50 can be disposed in an envelope formed from a first patch 61 and a second patch 63. Together, these patches 61, 63 define a compartment 65 which is sized and configured to receive the tubular enclosure 50 in its compressed state. A lubricant 67 can be disposed in the compartment 65 with the tubular enclosure 50.

In general, the patches 61, 63 can be formed from any material impervious to the lubricant 67. The material of the patches 61, 63 will perhaps be most dictated by the method in which the patches 61, 63 are to be attached to the belt 29. In a preferred embodiment wherein the belt 29 is formed from latex, the patches 61, 63 are formed from foil and attached to the respective sides 26 and 24 of the belt 29 for example by an adhesive 70 such as pharmaceutical glue. This is preferably a releasable attachment permitting the patches 61 and 63 to be removed in order to expose the tubular enclosure 50. Other means for sealing the patches 61, 63 to the belt 29 will be apparent but, importantly, removal of the patches 61, 63 must not damage the brief 23 or the tubular enclosure 50.

The brief 23 and the tubular enclosure 50 can be formed from the same material such as natural latex. However, other material such as synthetic latex, rubber, thermoplastic elastomers, and natural or synthetic woven fabrics may be advantageous in other embodiments. The tubular enclosure 50 may be formed with an integral relationship to the brief 23. Alternatively, a two-piece construction may be desired wherein the tubular enclosure 50 is heat-sealed, glued, sewn or otherwise attached to the brief 23.

The relative thickness of the various walls associated with the belt 29, the tube 52 and the cap 58 can be of importance to specific embodiments of the invention. In general, the thickness of the belt 29 can be dictated by the desirability for a generally low profile but with some degree of comfort and of course functionality. The thickness of the wall associated with the tube 52 is preferably as thin as possible to function as a sanitary barrier without sacrificing sensitivity. By comparison, the thickness of the cap 58, which can be integral with the tube 52, is generally greater in order that it might function as a semi-rigid anchor when used in the female anatomy. In this location, illustrated in FIG. 5, it is desirable that the tubular enclosure 50 be removably lodged within the female anatomy to anchor the second end 56 of the tube 52. Anchoring can also be enhanced by making the cap 58 larger in diameter than the tube 52. Providing the cap 58 with an increased thickness not only facilitates anchoring the tube 52 but also enhances the structure of the tubular enclosure at the point of greatest stress. In a preferred embodiment, the belt 29 has a thickness such as 1/16 inch, the wall of the tube 52 has a thickness such as 1/32 inch, and the wall of the cap 58 has a thickness such as 5/32 inch.

Figure 5:
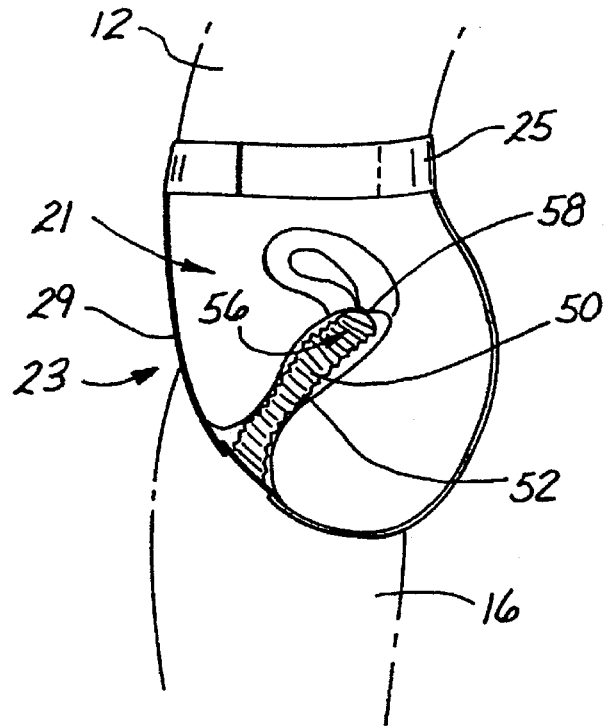
FIG. 5 is a side view of the garment operatively disposed with the tubular enclosure extending inwardly to accommodate a female anatomy.
Figure 6:
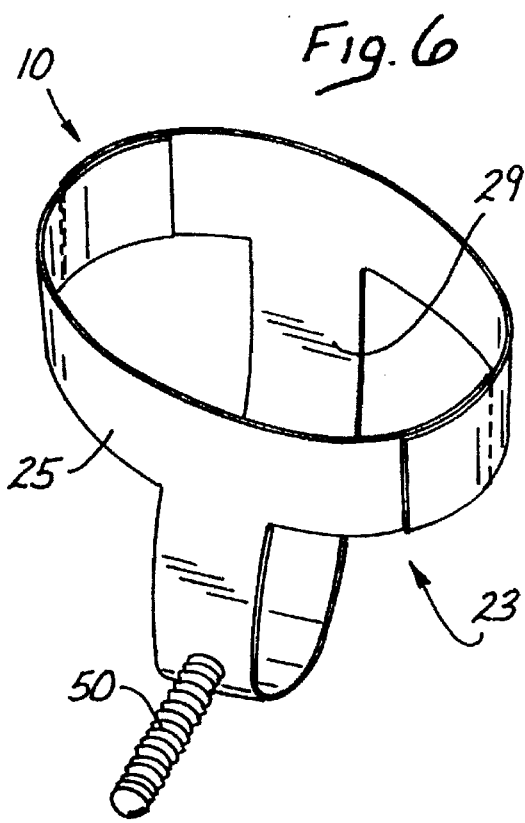
FIG. 6 is a side perspective view of the garment with the tubular enclosure extending outwardly to accommodate a male anatomy.

The invertibility or reversibility of the garment 10 is of particular interest as it enables the tubular enclosure 52 to function with either a male or female anatomy. When used with a female anatomy, the tubular enclosure extends inwardly of the brief 23 as illustrated in FIG. 5. When the garment 10 is adapted for use with the male anatomy, the tubular enclosure 52 extends outwardly of the brief 23 as illustrated in FIG. 6.

Figure 8:
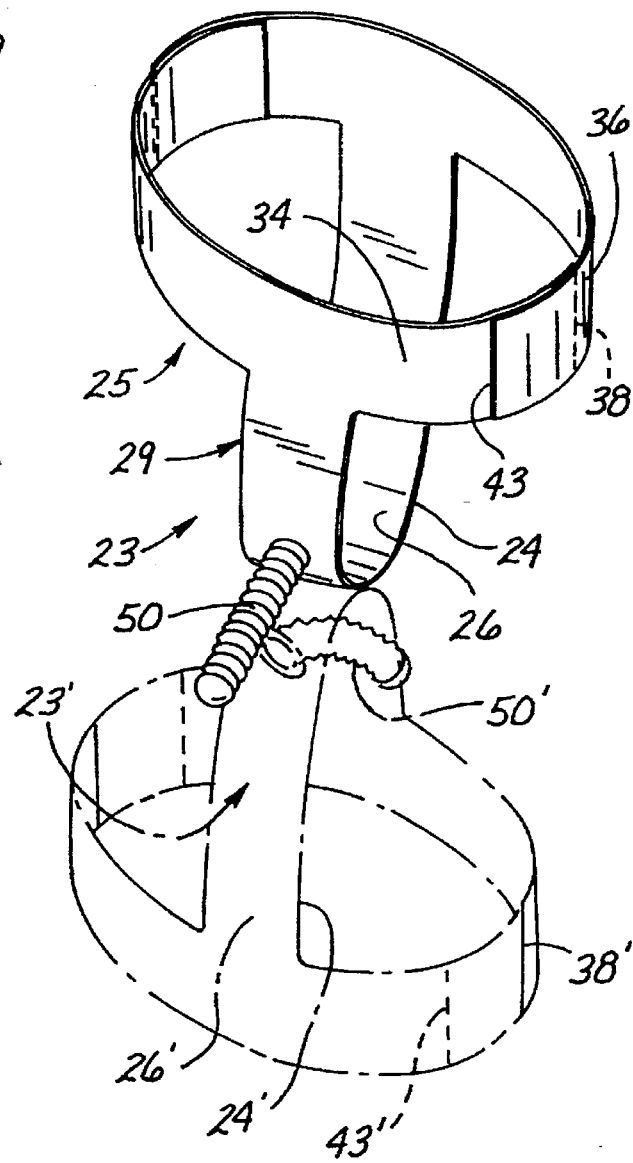
FIG. 8 is a side perspective view of the garment illustrating the reversibility of the brief to accommodate either a male or female anatomy.
Figure 7:
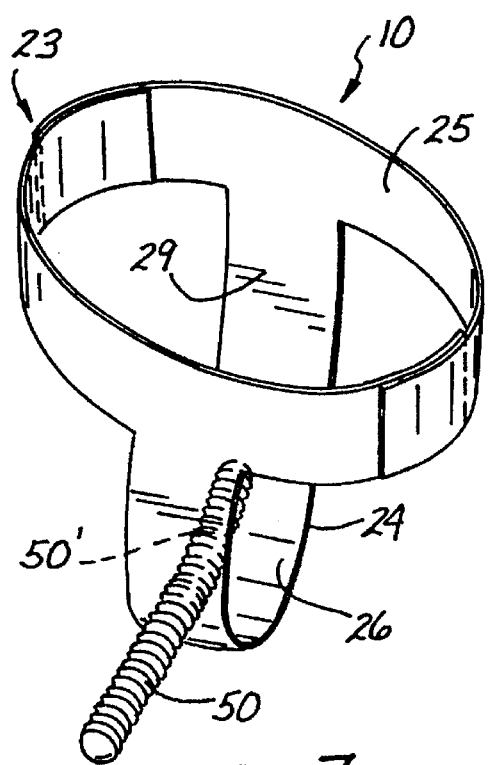
FIG. 7 is a side perspective view of the garment illustrating the reversibility of the tubular enclosure to accommodate either a male or female anatomy.

The reversibility of the garment 10 to provide for either the inward or outward extension of the tubular enclosure 50, is better understood with reference to FIG. 7 and 8. In these figures, components with a reversed orientation are designated by the same reference numeral followed by a prime sign. As illustrated in FIG. 7, the garment can be inverted by maintaining the brief 23 with a fixed disposition while inverting the tubular enclosure 50. For example, the enclosure 50 can be adapted to extend outwardly of the brief 23 in order to accommodate the male anatomy as illustrated by the solid lines 50 in FIG. 7. Alternatively, the tubular enclosure 50 can be inverted as shown by the dotted lines 50' to extend inwardly of the brief 23 in order to accommodate a female anatomy. In this method for inverting the garment 10, not only the tube 52, but also the cap 58 must be inverted.

The garment 10 can also be inverted as illustrated in FIG. 8 where the tubular enclosure has a generally fixed orientation with respect to the brief 23. In the illustrated case, the tubular enclosure 50 extends outwardly from the first side 24 of the brief 23. In this case, the inversion is accomplished by reversing the brief 23 as shown by the dotted lines 23' in FIG. 8. In this case, the inversion of the brief 23' moves the first side 24' from the outer surface to the inner surface of the brief 23'. With the tubular enclosure 50 having a fixed orientation with the brief 23, it moves from an orientation which extends outwardly, as the brief 23 is inverted.

While the normal stretch of the elastomeric waist belt 25 may be sufficient to enable the garment 10 to be easily positioned, the preferred embodiment illustrated in FIG. 2, provides for separation of the waist belt 25 into the two waist sections 34, 36. In such an embodiment, the brief 23 is most easily inverted by separating the two waist sections 34, 36 and reconnecting them in the inverted configuration shown by the dotted lines 23'. In this case, the ends 38' and 43' of the respective waist sections 36' and 34' will be reversed as shown by the reference numerals 38' and 43' in FIG. 8.

Many different variations on the foregoing embodiments are possible. Certainly different materials can be used for the various components in order to accentuate features such as comfort for the brief, safety for the tube 52, and anchoring for the cap 58. The various components can also be separately manufactured and joined by heat sealing or adhesion. As noted, in a preferred embodiment, the brief 23 and tubular enclosure 50 are formed with an integral construction. Various apparatus for portably packaging the tubular enclosure 50 in its compressed state will also be apparent. The patches 61 and 63 can be formed from different materials to facilitate features such as comfort and removability.

From the foregoing discussion it will also be apparent that maximum protection against conception and disease communication can be achieved when each of the participants wears a garment 10. Whereas conception and disease preventative devices of the past are well-known to have a failure rate between 6% and 10%, this rate is drastically reduced to about 1% where one garment protects the male anatomy while the second garment protects the female anatomy. The reversibility of the garment 10 ensures that only a single structure need be manufactured since this single structure can be adapted to both the male and female anatomies. This is true in spite of differences in the location of the respective anatomies relative to the waist 14. These variations seem to be easily accommodated by the elastomeric characteristics of not only the tubular enclosure 50, but also the brief 23.

Given these wide variations, which are all within the scope of this concept, one is cautioned not to restrict the invention to the embodiments which have been specifically disclosed and illustrated, but rather, encouraged to determine the scope of the invention only with reference to the following claims.

I claim:

1. A body garment adapted to be worn by either a male or a female user have a waist and an abdominal area, comprising:
    a brief having a first side and a second side and being sized and configured to be worn over the abdominal area of either the male or female user, the brief including a waste band and a crotch section;
    a tubular enclosure forming a sanitary barrier and having a closed end and an opened end, the closed end being alternatively configured to extend on the first side of the brief or on the second side of the brief and the open end being coupled to the crotch section of the brief, the tubular enclosure having an elongated state and a collapsed state,
    wherein the tubular enclosure includes:
        a tube having a generally cylindrical wall with a first uniform thickness; and
        a cap coupled to the tube at the closed end of the tubular enclosure and consisting of a wall with a second uniform thickness greater than the first thickness of the wall of the tube, said brief has an envelope attached thereto, said envelope further comprises a first patch sealed to the brief around the tubular enclosure on the first side of the brief.

2. The garment recited in claim 1 wherein the brief has a
    a second wall sealed to the brief around the tubular enclosure on the second side of the brief; and
    the first wall and the second wall defining the compartment of the envelope.

3. The garment recited in claim 1 wherein the user has a pair of legs and the garment further comprises:
    a first belt included in the waist band of the brief, the first belt being sized and configured to extend around the waist of the user;
    a second belt included in the crotch section of the brief, the second belt being sized and configured to extend between the legs of the user.

4. The garment recited in claim 3 wherein the tubular enclosure and the second belt are integrally formed from elastic material.

5. A body garment adapted to be worn by a user having a waist and an abdominal area, the garment comprising:
    a brief sized and configured to be worn over the abdominal area of a user, the brief including a waist band and a crotch section with a first side and a second side;
    a tubular enclosure forming a sanitary barrier and having a closed end and an opened end, the tubular enclosure being invertible to extend from either the first side or second side of the crotch section the open end being coupled to the crotch section of the brief;
    the tubular enclosure being integral with at least the crotch section of the brief,
    wherein the tubular enclosure further comprises:
        a tube having a first end, a second end, and a wall with a first thickness, the first end of the tube being attached to the brief;
        an end cap disposed to close the second end of the tube and to form with the tube the tubular enclosure;
        the end cap having a wall with a second thickness greater than the first thickness of the wall of the tube, the wall of the end cap being integral with the wall of the tube, wherein said brief has a first side and a second side and an envelope, said envelope further comprises a first patch disposed to removably cover the tubular enclosure in the collapsed state.

6. The garment recited in claim 5 wherein the tubular enclosure has an extended state and a collapsed state and the garment further comprises:
    said envelope is disposed in sealing engagement with the crotch section of the brief and defining a compartment sized and configured to receive the tubular enclosure in the collapsed state.

7. The garment recited in claim 6 wherein the brief has a
    a first seal formed between the first patch and the crotch section of the brief;
    a second patch disposed to removably cover the tubular enclosure in the collapsed state; and a second circumferential seal disposed to couple the second patch to the second side of the brief.

8. The garment recited in claim 7 wherein the first patch and the second patch form the compartment of the envelope, and the garment further comprises, a lubricant disposed in the compartment of the envelope with the tubular enclosure.

9. A reversible protective garment, comprising:

a brief configurable to be worn by either a male user or a female user, the brief having a first side and a second side;

an elastomeric tube having a first end, and a second end, and being extensible from a collapsed state to an extended state;

means for attaching the first end of the tube to the brief;

a cap disposed to fully enclose the second end of the tube;

one of the tube and the brief being invertible to reverse the garment in order to alternatively accommodate a male anatomy, wherein said brief has a first patch sealed to the brief around the tubular enclosure on the first side of the brief and a female anatomy.

10. The device recited in claim 9 wherein the brief is disposed with the first side of the brief in contact with the user and the tubular enclosure is invertible so that in its extended state the tubular enclosure is extensible alternatively from one of the first side of the brief to accommodate a female anatomy and the second side of the brief to accommodate a male anatomy.

11. The device recited in claim 10 wherein the tubular enclosure extends from the first side of the brief.

12. The device recited in claim 9 wherein:

the tubular enclosure has a first side and a second side;

the tube in the extended state extends from the first side of the brief;

the brief is reversible between a first state and a second state;

the brief in the first state is characterized by the first surface of the brief facing inwardly and the tube extending inwardly of the brief to accommodate a female anatomy; and the second state of the brief is characterized by the second surface of the brief facing inwardly and the tube extending outwardly of the brief to accommodate a male anatomy.

13. A. A protective garment configurable between five modes of operation, the protective garment comprising:

(a) a brief sized and configured to be worn over an abdominal area of a user, the brief including:
  (1) a first side;
  (2) a second side; and
  (3) an aperture connecting the first side of the brief to the second side of the brief, the aperture being defined by a circumferential parameter;

(b) a bellows elastomeric tube being extensible from a collapsed state to an extended shape, the bellows elastomeric tube having a first thickness and including:
  (1) an outer end; and
  (2) an inner end having a circumferential perimeter; and
  (3) a bellows cylindrical portion connecting the outer end of the bellows elastomeric tube to the inner end of the bellows elastomeric tube, the cylindrical portion enabling the bellows elastomeric tube to function equally well when a first surface of the bellows elastomeric tube is an inner surface of the bellows elastomeric tube and when the first surface of the bellows elastomeric tube is an outer surface of the bellows elastomeric tube;

(c) means for attaching the circumferential perimeter of the inner end of the bellows elastomeric tube to the circumferential perimeter surrounding the aperture of the brief; and (d) a cap connected to the outer end of the bellows elastomeric tube, the cap having a second thickness which is greater than the first thickness of the bellows elastomeric tube, wherein said brief has a first patch sealed to the brief around the tubular enclosure on the first side of the brief, (e) wherein the protective garment is configurable between a first mode and a second mode for a female user, an between a third mode and a fourth mode for a male user, and (f) wherein the five modes of operation are defined as follows:
  (1) the first mode of operation configuring the first side of the brief to be worn over the abdominal area of the female user and configuring the outer end of the bellows elastomeric tube to extend inward into a female anatomy of the female user;
  (2) the second mode of operation configuring the second side of the brief to be worn over the abdominal area of the female user and configuring the outer end of the bellows elastomeric tube to extend inward into the female anatomy of the female user;
  (3) the third mode of operation configuring the first side of the brief to be worn over the abdominal area of the male user and configuring the outer end of the bellows elastomeric tube to extend outward over a male anatomy of the male user;
  (4) the fourth mode of operation configuring the second side of the brief to be worn over the abdominal area of the male user and configuring the outer end of the bellows elastomeric tube to extend outward over a male anatomy of the male user; and
  (5) the female user wearing the protective garment in one of the first or the second mode and the male user wearing a duplicate of the protective garment in one of the third and the fourth mode, both the male and female wearing duplicates of the same protective garment in different configurations at the same time during intercourse between the female user and the male user.

* * * * *